United States Patent
Lee et al.

(10) Patent No.: US 8,124,832 B2
(45) Date of Patent: Feb. 28, 2012

(54) METHOD FOR PRODUCING CLONED DOG

(75) Inventors: Byeong Chun Lee, Seoul (KR); Sung Keun Kang, Seoul (KR); Dae Yong Kim, Seoul (KR); Min Kyu Kim, Seoul (KR); Goo Jang, Seoul (KR); Hyun Ju Oh, Seoul (KR); M. Shamim Hossein, Seoul (KR); Fibrianto Yuda, Seoul (KR); Hye Jin Kim, Seoul (KR); So Gun Hong, Seoul (KR); Jung Eun Park, Seoul (KR); Joung Joo Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 11/762,077

(22) Filed: Jun. 13, 2007

(65) Prior Publication Data

US 2008/0295191 A1    Nov. 27, 2008

(30) Foreign Application Priority Data

Jan. 17, 2007  (KR) .................. 10-2007-0005350

(51) Int. Cl.
*A01K 67/027* (2006.01)
*C12N 15/00* (2006.01)

(52) U.S. Cl. ................. 800/24; 800/14; 800/13
(58) Field of Classification Search .............. 800/24
See application file for complete search history.

(56) References Cited

U.S. PATENT DOCUMENTS

| | | | |
|---|---|---|---|
| 4,994,384 A | 2/1991 | Prather et al. | |
| 5,057,420 A | 10/1991 | Massey | |
| 5,945,577 A | 8/1999 | Stice et al. | |

FOREIGN PATENT DOCUMENTS

| | | | |
|---|---|---|---|
| EP | 0930009 A1 | 7/1999 | |
| KR | 1020010005423 A | 1/2001 | |
| KR | 1020010069215 A | 7/2001 | |
| KR | 1020070013432 A | 1/2007 | |
| WO | 9901164 A1 | 1/1999 | |
| WO | 9934669 A1 | 7/1999 | |
| WO | 9937143 A2 | 7/1999 | |
| WO | WO 2004085631 A2 * | 10/2004 | |
| WO | WO 2007013763 A1 * | 2/2007 | |

OTHER PUBLICATIONS

Fehilly, C et al., 1984, Nature, 307:634-636.*
Meirelles, FV et al, 2001, Genetics, 158:351-356.*
Lee, J-W, 2004, Mol Reprod Dev, 68:51-57.*
Fehilly,J Reprod Fert, 1985, 74:215-221.*
Early embryonic development in vitro and embryo transfer in the cat. Kanda et al, J. Vet. Med. Sci. 57(4): 641-646, 1995.
Nuclear transplantation in sheep embryos. Willadse, Nature, 320:63-65, 1986.
Nuclear transfer of porcine embryos using cryopreserved delipated blastomeres as donor nuclei. Nagashima et al., Mol. Reprod. Dev. 48. 339-343 1997.
Nuclear transplantation in early pig embryos. Prather et al., Biol. Repord. 41: 414-418, 1989.
Nuclear transplantation in early pig embryo: nuclear swelling. Prather et al., J. Exp. Zool. 255:355-358, 1990.
In vitro development of nuclear transplant pig embryos. Terlouw et al., Theriogenology 37: 309, 1992.
Plasma LH and progesterone levels before and after ovulation and observation of ovarian follicles by ultrasonographic diagnosis system in dogs. Hase et al., J. Vet. Med. Sci, 62: 243-248, 2000.
Development of bovine embryos in vitro as affected by energy substrates. Charles Rosenkrans ; Rosenkrans et al., Biol. Repord. 49, 459-462, 1993.
Effect of glycosaminoglycans on the preimplantation development of embryos derived from in vitro fertilization and somatic cell nuclear transfer. G. Jang et al., Repord. Fertil. Dev., 15, 179-185, 2003.

* cited by examiner

*Primary Examiner* — Valarie Bertoglio
(74) *Attorney, Agent, or Firm* — Hershkovitz & Associates, LLC; Abraham Hershkovitz (57) ABSTRACT

Provided is a method for producing a cloned dog by enucleating an oocyte of a dog to produce an enucleated oocyte, transferring a somatic cell of the dog into the enucleated oocyte, carrying out electrofusion under optimized conditions to produce a nuclear transfer embryo, and transferring the nuclear transfer embryo into its surrogate mother.

2 Claims, 2 Drawing Sheets

METHOD FOR PRODUCING CLONED DOG

CROSS-REFERENCE TO RELATED APPLICATION

This application claims the benefit of Korean Patent Application No. 2007-0005350, filed Jan. 17, 2007, the contents of which are hereby incorporated herein by reference in their entirety.

BACKGROUND OF THE INVENTION

1. Field of the Invention

The present invention relates to a method for producing a cloned dog. More particularly, the present invention relates to a method for producing a cloned dog by enucleating an oocyte of a dog to prepare an enucleated oocyte, transferring a somatic cell of the dog into the enucleated oocyte and electrofusing it under optimized conditions to prepare a nuclear transfer embryo, and transferring the nuclear transfer embryo to an oviduct of its surrogate mother.

2. Description of the Related Art

With the recent development of somatic cell nuclear transfer technology by cell fusion or intracytoplasmic cell injection, animals are actually being cloned.

The somatic cell nuclear transfer technology, which allows living offspring to be born without undergoing meiosis and haploid germ cell which generally occur in a generative process, is a method of developing new individuals by transferring diploid somatic cells of adults into enucleated cells to produce embryos and transferring the embryos in vivo. Generally, in somatic cell nuclear transfer technology, recipient oocytes of somatic cell donor nuclei are used after they are artificially cultured in vitro to metaphase II of meiosis. Then, in order to prevent the development of chromosomal abnormality resulting from the somatic cell nuclear transfer, the mature oocytes are enucleated before transferring the somatic cells. After transferring the somatic cells into the perivitelline space or cytoplasm of the mature oocytes, the enucleated oocytes and the somatic cells are physically fused with each other by electrical stimulation. The fused enucleated oocytes and the somatic cells are activated by electrical stimulation or chemical substances and transferred into surrogate mothers to produce living offspring.

Such somatic cell nuclear transfer technology can be widely used in the field, for example, in the propagation of superior animals, conservation of rare or nearly extinct animals, production of certain nutrients, production of therapeutic bio-materials, production of animals for organ transplantation, production of animals with diseases or disorders, and production of medically worthy animals for alternative treatments to organ transplantation such as gene therapy.

Animal cloning was first accomplished by Dr. Wilmut of the Roslin Institute, England, by taking a mammary gland cell from a six-year old sheep, transferring the cell into an enucleated oocyte to prepare a nuclear transfer embryo, and transferring the embryo in vivo, thereby producing a cloned animal named Dolly. Thereafter, it was reported that cloned cows, mice, goats, pigs and rabbits were produced by nuclear transfer using somatic cells (see WO 9937143 A2, EP 930009A1, WO 9934669A1, WO 9901164A1 and U.S. Pat. No. 5,945,577).

Meanwhile, not only cloning of farm animals such as cows and pigs, but recent cloning of pet animals such as dogs has also attracted a great deal of interest. A cat was the first pet animal to be cloned, and a study on dog cloning was conducted with several millions of dollars in funding.

However, it is very difficult to implement cloning by somatic cell nuclear transfer due to species-specific generative properties of the dog. The present inventors produced a cloned dog for the first time, but many difficulties remained in putting such cloning into practical use because the cloning efficiency was too low.

Accordingly, while researching an improved method for producing a cloned dog using somatic cell nuclear transfer, the present inventors have established optimized electrofusion conditions of the enucleated oocyte and the nuclear donor cell, produced a nuclear transfer embryo, and transferred the nuclear transfer embryo into a surrogate mother to produce a cloned dog with high efficiency, thereby completing the present invention.

SUMMARY OF THE INVENTION

It is therefore an object of the invention to provide a method for producing a nuclear transfer embryo of a dog using somatic cell nuclear transfer technology, characterized in that the nuclear transfer embryo is produced under optimized fusion conditions.

It is another object of the invention to provide a nuclear transfer embryo of a cloned dog produced by the method.

It is yet another object of the invention to provide a method for producing a cloned dog, which comprises transferring the nuclear transfer embryo into its surrogate mother to give birth to living offspring.

To achieve the above objects, in one aspect, the present invention provides a method for producing a nuclear transfer embryo of a dog using somatic cell nuclear transfer technology, characterized in that the nuclear transfer embryo is produced under optimized fusion conditions.

In another aspect, the present invention provides a nuclear transfer embryo of a cloned dog produced by the method.

In yet another aspect, the present invention provides a method for producing a cloned dog, which comprises transferring the nuclear transfer embryo into its surrogate mother to give birth to living offspring.

BRIEF DESCRIPTION OF THE DRAWINGS

The foregoing and other objects, features and advantages of the invention will become apparent from the following more particular description of exemplary embodiments of the invention, as illustrated in the accompanying drawings. The drawings are not necessarily to scale, emphasis instead being placed upon illustrating the principles of the invention.

DETAILED DESCRIPTION OF THE INVENTION

The present invention will now be described more fully hereinafter with reference to the accompanying drawings, in which exemplary embodiments of the invention are shown.

Definitions of Terms

The term "nuclear transfer" as used herein refers to a gene manipulation technique allowing an identical characteristic form and quality acquired by artificially combining an enucleated cell with nuclear DNA of one cell.

The term "nuclear transfer embryo" as used herein refers to an embryo injected or fused with a nuclear donor cell.

The term "cloning" as used herein refers to a gene manipulation technique for preparing a new individual unit having a gene set identical to another individual unit. In particular the term "cloned" is used herein to mean that a cell, an embryonic cell, a fetal cell, and/or an animal cell has a nuclear DNA sequence substantially similar or identical to the nuclear DNA sequence of another cell.

The term "nuclear donor cell" as used herein refers to a cell or a nucleus from the cell which transfers the nucleus into a recipient oocyte functioning as a nuclear acceptor.

The term "recipient oocyte" as used herein refers to an oocyte which receives a nucleus from a nuclear donor cell after its nucleus has been removed through enucleation.

The term "oocyte" as used herein refers to a mature oocyte which has preferably reached the metaphase of meiosis.

The term "enucleated oocyte" as used herein refers to an oocyte which has had its nucleus removed.

The term "fusion" as used herein refers to a combination between a nuclear donor cell and a lipid membrane of a recipient oocyte. For example, the lipid membrane may be the plasma membrane or nuclear membrane of cells. The fusion may occur upon generation of electrical stimulus between a nuclear donor cell and a recipient oocyte when they are placed adjacent to each other or when a nuclear donor cell is placed in a perivitelline space of the recipient oocyte.

The term "activation" as used herein refers to stimulation of a cell to divide, before, during or after nuclear transfer. Preferably, in the present invention, it means stimulation of a cell to divide after the nuclear transfer.

The term "living offspring" as used herein refers to an animal which can survive ex utero. Preferably, it is an animal which can survive for one second, one minute, one day, one week, one month, six months, or more than one year. The animal may not require an in utero environment for survival.

The present invention is characterized in that electrofusion conditions of a nuclear transfer embryo are optimized when a dog is cloned using somatic cell nuclear transfer technology to produce the nuclear transfer embryo of the dog, and the nuclear transfer embryo is transferred into an oviduct of its surrogate mother to produce living offspring, so that cloning efficiency is significantly enhanced.

To detail this, a method for producing a nuclear transfer embryo of a canine includes: producing an enucleated oocyte; producing a nuclear donor cell; micro-injecting and electrofusing the nuclear donor cell; and activating the electrofused oocyte, wherein the electrofusion is carried out under a condition of 3.8 to 5.0 kV/cm.

Each step of the inventive method for producing a canine nuclear transfer embryo will be described in detail below.

Step 1: Enucleation of Recipient Oocytes

The recipient oocytes may be immature oocytes, mature oocytes, slightly aged oocytes, moderately aged oocytes, or very aged oocytes of canines. Preferably, immature oocytes collected from canines may mature in vitro, or oocytes matured in vivo may be collected. Generally, oocytes of mammals (e.g., cattle, pigs and sheep) are ovulated in mature oocytes, i.e., metaphase II stage of meiosis, whereas canine oocytes are ovulated at prophase I stage of meiosis, unlike other animals, and mature within the oviduct for 48 to 72 hours. Because the maturation rate of canine oocyte nuclei is very low and the ovulation time and reproductive physiology of canines are different from other animals, canine oocytes matured in vivo are preferably collected for use as recipient oocytes.

More specifically, the collection of mature oocytes from canines is preferably conducted at 48-72 hours, and more preferably, at 72 hours after ovulation induction in the canines. The day of ovulation in canines may be determined by any method well known in the art. Examples of the method of determining the day of ovulation may include, but are not limited to, vaginal smear tests, measurement of serum sex hormone levels, and use of ultrasonographic diagnosis systems. The start of estrus in canines can be confirmed by vulva swelling and serosanguinous discharge.

In one example of the present invention, a vaginal smear test and the analysis of serum progesterone concentration were conducted; the day on which nonkeratinized epithelial cells reached more than 80% and serum progesterone concentration reached about 4.0-7.5 ng/mL was regarded as the day of ovulation. Meanwhile, maturation time of oocytes ovulated from canine is known to be 48-72 hours after ovulation; the present inventors analyzed oocytes collected at 48 hours, 60 hours and 72 hours after ovulation, and as a result, it was confirmed that oocytes collected at about 72 hours after ovulation are mature oocytes corresponding to metaphase II of meiosis. Therefore, it was concluded that it is most preferable to collect mature oocytes from canines at 72 hours after ovulation.

As a method of collecting oocytes matured in vivo, a surgical method including anesthetizing an animal followed by laparotomy can be used. More specifically, oocytes matured in vivo can be collected using salpingectomy by any method well known in the art. Salpingectomy is a method of collecting the oocytes by surgically excising the oviduct, flushing the oviduct with an oocyte collection fluid to obtain a flushed solution, and collecting the oocytes from the flushed solution.

In addition, oocytes matured in vivo can be collected by inserting a catheter into the fimbriated end of the oviduct, and injecting a flushing fluid into the uterotubal junction using a needle indwelling catheter. This method has the advantage of not damaging the oviduct, and thus allowing the oocyte donor animal to be used for a subsequent estrus.

Figure 1:
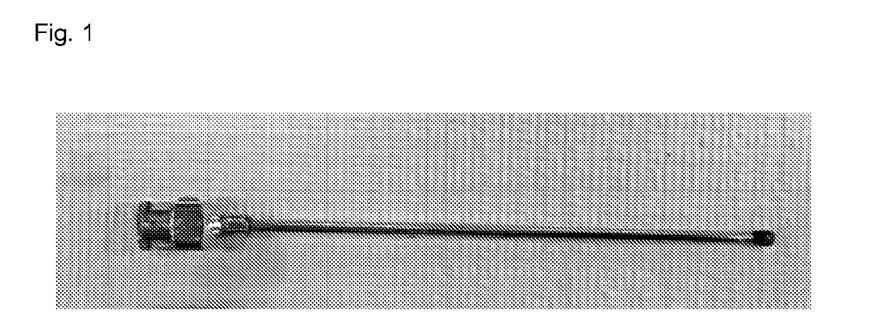
FIG. 1 is a photograph illustrating an 18 gauge needle needed for retrieving an oocyte from a dog in accordance with an exemplary embodiment of the present invention.

Accordingly, the oocytes matured in vivo are preferably collected by the method using the catheter which does not cause the oviduct to be damaged. Meanwhile, in order to increase oocyte collection rate in the oocyte collection method using the catheter, the present inventors have developed an oocyte retrieval needle which has a rounded front end such that it is easily inserted into the entrance of the oviduct (see FIG. 1). More specifically, a method of collecting oocytes using the needle having a rounded front end developed by the present inventors comprises inserting and ligating the oocyte retrieval needle in the oviduct, followed by flushing the uterotubal junction downward with oocyte collection fluid and into the oocyte retrieval needle, and observing the flushed solution with a microscope to select mature oocytes.

After the collection of mature oocytes, the haploid nuclei of the oocytes are removed. Enucleation of the oocytes can be performed by any method well known in the art (see U.S. Pat. No. 4,994,384; U.S. Pat. No. 5,057,420; U.S. Pat. No. 5,945, 577; EP Pat. No. 0930009 A1; Korean Pat. No. 342437; Kanda et al, J. Vet. Med. Sci, 57(4):641-646, 1995; Willadsen, Nature, 320:63-65, 1986, Nagashima et al., Mol. Reprod. Dev. 48:339-343 1997; Nagashima et al., J. Reprod. Dev. 38:37-78, 1992; Prather et al., Biol. Reprod. 41:414-418, 1989, Prather et al., J. Exp. Zool. 255:355-358, 1990; Saito et al., Assis Reprod Tech Andro, 259:257-266, 1992; Terlouw et al., Theriogenology 37:309, 1992).

Preferably, the enucleation of recipient oocytes can be performed by either of the following two methods. One method comprises removing the cumulus cells of mature recipient oocytes, incising a portion of the zona pellucida of the recipient oocytes using a microneedle to give a slit, and removing the first polar body, nucleus and adjacent cytoplasm (the smallest possible amount) through the slit. The other method comprises removing the cumulus cells of recipient oocytes, staining the oocytes, and removing the first polar body and nucleus of the oocytes using an aspiration pipette. More preferably, for the enucleation of oocytes, the aspiration method is used for oocytes with a high chance of survival, and the method of forming the slit is used for oocytes with a low chance of survival, decided by visual evaluation of recipient oocytes.

Step 2: Preparation of Nuclear Donor Cells

Somatic cells derived from canines can be used as nuclear donor cells. Specifically, somatic cells used in the present invention may be canine embryonic cells, fetal cells, juvenile cells, or adult cells that preferably originate from tissue such as the cumulus, skin, oral mucosa, blood, bone marrow, liver, lungs, kidneys, muscles, reproductive tract, etc. Examples of somatic cells which can be used in the present invention may include, but are not limited to, a cumulus cell, an epithelial cell, fibroblast, a neural cell, an epidermal cell, keratinocyte, a hematopoietic cell, melanocyte, chondrocyte, erythrocyte, macropharge, monocyte, a muscle cell, B lymphocyte, T lymphocyte, an embryonic stem cell, and an embryonic germ cell. More preferably, somatic cells which can be used in the present invention may include fetal fibroblast, adult fibroblast, and a cumulus cell.

Furthermore, the nuclear donor cells used in the present invention may be obtained by transforming wild-type somatic cells with certain genes by a gene transfer method or a gene targeting method. The gene transfer or gene targeting method is well known among those skilled in the art.

The somatic cells which are provided as the nuclear donor cells can be obtained by a method of preparing surgical samples or biopsy samples, and single cells can be obtained from the samples by any method well known in the art. For example, some of tissue from an animal to be cloned is aseptically incised to obtain a surgical sample or a biopsy sample, and the sample is minced, treated with trypsin and then cultured in a tissue culture medium. After culturing for 3-4 days in the tissue culture medium, the growth of the cells on a culture dish is confirmed. When the cells are completely grown, some of the tissue is frozen and stored in liquid nitrogen for later use, and the remnants are subcultured for use in nuclear transfer. The cells to be continuously cultured for use in nuclear transfer are subcultured up to 10 times to prevent excessive growth.

The tissue culture medium may be any that is well known in the art, for example, TCM-199 or DMEM (Dulbecco's Modified Eagle's Medium).

Step 3: Microinjection and Fusion of Nuclear Donor Cells

The microinjection of nuclear donor cells into enucleated oocytes is performed by microinjecting the nuclear donor cells between the cytoplasm and zona pellucida of the enucleated oocytes by using a transfer pipette.

The enucleated oocytes microinjected with nuclear donor cells are electrically fused with nuclear donor cells, by using a cell Manipulator. The current of the electrical fusion may be an alternate or direct current, and the electrical fusion can be performed using a needle-type electrode under a condition of 3.8 to 5.0 kV/cm for 15 to 25 μs, more particularly, under a condition of 3.8 to 4.2 kV/cm, and most preferably, it can be performed two times under a condition of 4.0 kV/cm.

The fusion of nuclear donor cells to oocytes by electrical stimulation can be performed in a fusion medium. The fusion medium used in the present invention may be a medium containing mannitol, $MgSO_4$, Hepes and BSA.

Step 4: Activation of Nuclear Transfer Embryos

Activation of the fused nuclear transfer embryos is a step of reactivating the temporarily paused cell-cycle. To this end, the activation of cell signal delivery materials of pausing elements of cell-cycle such as MPF, MAP kitase etc. has to be reduced. Generally, methods of activating the nuclear transfer embryos include an electrical method and a chemical method. In the present invention, it is preferable to activate the nuclear transfer embryos by the chemical method. The chemical method can hasten activation of nuclear transfer embryos compared to the electrical method. As the chemical method, there is a method of treating nuclear transfer embryos with material such as ethanol, inositol trisphosphate, bivalency ion (e.g., $Ca^{2+}$ or $Sr^{2+}$), microtubule inhibitors (e.g. cytochalasin B), bivalency ion ionophore (e.g., $Ca^{2+}$ ionophore enomicin) and protein kinase inhibitors (e.g., 6-dimethylaminopurine), protein synthesis inhibitors (e.g., cy-cloheximide), phorbol 12-myristate 13-acetate.

Preferably, as the chemical method for the activation of nuclear transfer embryos, a method of treating the nuclear transfer embryos simultaneously or stepwise with calcium ionophore and 6-dimethylaminopurin can be used in the present invention. More preferably, the nuclear transfer embryos are treated with 5-10 μM calcium ionophore at 37 to 39° C. for 3 to 6 minutes and then with 1.5 to 2.5 mM 6-dimethylaminopurin at 37 to 39° C. for 4 to 5 hours.

In another aspect, the present invention provides nuclear transfer embryos of the dog prepared by the above-described method. The present inventors named the nuclear transfer embryos of the dog prepared in accordance with an embodiment of the present invention, SNU-BONA (cloned embryos), and deposited them with an international depositary authority, KCTC (Korean Collection for Type Cultures; Korean Research Institute of Bioscience and Biotechnology, 52, Eoeun-dong, Yuseong-gu, Daejeon, Korea) on Nov. 27, 2006, under the accession number KCTC 11037BP. The nuclear transfer embryos may be freeze-stored and used after dissolution, if necessary.

Furthermore, the canine nuclear transfer embryos according to the present invention can be used to produce cloned canines by transferring them into surrogate mothers to give birth to living offspring. Preferably, the transfer of the inventive nuclear transfer embryos into surrogate mothers is performed by transferring the nuclear transfer embryos into the oviduct of the surrogate mothers. The transfer can be performed by any method well known in the art, and preferably, a catheter can be used to transfer the cloned embryos.

In an embodiment of the present invention, 3 cloned dogs were first produced by transferring the inventive nuclear transfer embryos into the oviducts of surrogate mothers (see embodiment 6).

Meanwhile, in the transfer of the nuclear transfer embryos into surrogate mothers, the nuclear transfer embryos may be at the 1-cell, 2-cell or 4-cell stage. To this end, it is preferable to perform the transfer of the nuclear transfer embryos into the surrogate mothers within 4 hours after activation. Also, the nuclear transfer embryos can be cultured in 25 μl (microdrops) of mSOF overlaid with mineral oil until surrogate mothers are prepared.

Three cloned dogs were produced from 12 surrogate mothers in total using 167 nuclear transfer embryos in accordance with the present invention (1.8%; see Experimental example 3). Therefore, the method of the present invention can be applied to actual production of cloned dogs by improving upon drawbacks of the methods well known in the art such as low cloning efficiency.

Figure 3:
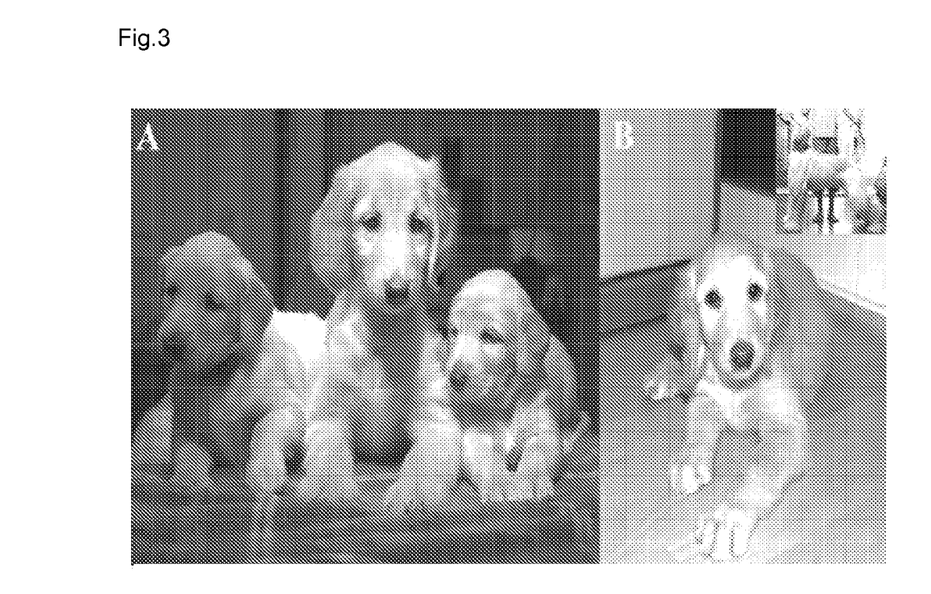
FIG. 3 illustrates a photograph (A) of three cloned dogs and a photograph (B) of a somatic cell donor in accordance with an exemplary embodiment of the present invention.

The cloned dogs produced by the method of the present invention have phenotypes similar to the nuclear donor cells or donors (see FIG. 3), and have exactly the same genetic characteristics as nuclear donor cells or donors. In an embodiment of the present invention, cloned dogs were produced according to the inventive method and analyzed for their genetic characteristics using microsatellite analysis (see experimental example 1). As a result, it could be seen that the cloned dogs according to the present invention had exactly the same genetic characteristics as nuclear donor cells or donors (see Table 8).

In addition, production of the three female cloned dogs, rather than the conventional male cloned dogs, was first accomplished by the present inventors. Therefore, reproductive characteristics of the cloned dogs can be more exactly researched by mating and pregnancy.

Hereinafter, embodiments of the present invention will be described in detail.

However, the following embodiments are only illustrative and do not limit the scope of the present invention.

Embodiment 1

Collection of Recipient Oocytes from Dogs

Figure 2:
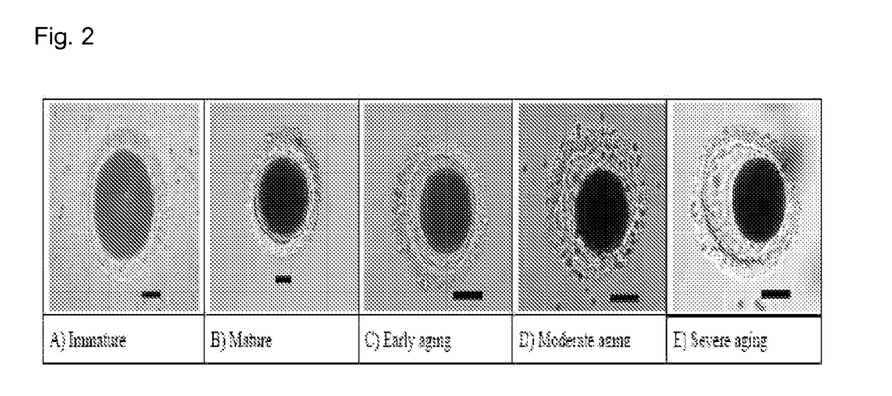
FIG. 2 illustrates various phases of an in vivo mature oocyte flushed from an oviduct of an oocyte donor dog at about 72 hours after ovulation (scale bar=40 μm).

Dogs used as oocyte donors were 23 mixed breed female dogs aged 1 to 5 years. These dogs were kept according to the standards established by the Seoul National University for Accreditation of Laboratory Animal Care. Ovulation timing was determined by performing a vaginal smear test and measuring serum progesterone concentration on naturally estrus dogs every day, and mature oocytes were retrieved by performing an operation at 48-72 hours after ovulation. The retrieved oocytes included immature oocytes, mature oocytes, slightly aged oocytes, moderately aged oocytes, and very aged oocytes. Shapes of these oocytes are shown in FIG. 2.

In order to measure serum progesterone concentration, 3 to 5 ml of blood was collected everyday and centrifuged to obtain serum, and the serum was analyzed using a DSL-3900 ACTIVE Progesterone Coated-Tube Radioimmunoassay Kit (Diagnostic Systems Laboratories, Inc., USA). The day on which the progesterone concentration initially reached 4.0 to 7.5 ng/ml was considered the day of ovulation. (Hase et al., J. Vet. Med. Sci, 62:243-248, 2000).

To perform the vaginal smear test, smears were obtained daily from the day of the initial sign of proestrus. Smear samples were collected by inserting a swab into the lips of the vulva, and then rolled on a slide glass. After staining with a Diff-Quik staining (International chemical Co., Japan), the smears were examined with a microscope; the time at which superficial cells reached more than 80% of the epithelial cells cornified index (Evans J. M. et al., Vet. Rec., 7:598-599, 1970) was regarded as the time of ovulation.

The present inventors checked the ovulation time in accordance with the above-described method, and retrieved oocytes from dogs by means of laparotomy by the following method.

First, 6 mg/kg of ketamine HCl and 1 mg/kg of xylazine were administered to anesthetize a female dog as an oocyte donor, and isoflurance was administered to keep the anesthetized state.

A needle (18 gauge, 7.5 cm, see FIG. 1) with a rounded front end was inserted into the fimbriated end of the oviduct through a bursal slit of the anesthetized dog. The inserted needle was fixed by a suture. To this end, a quick-release device using a 3 cm plastic tube (diameter: 2 mm) and a hermostatic forceps was employed. In order to make the catheter of the oviduct seen better, a digital pressure was applied to the oviduct and a lower portion of a junction between the uterus-oviduct, and a catheter (24 gauge) was inserted into the vein to flush out the oocytes with the Hepes-buffer tissue culturing medium TCM-199 (i.e., medium for oocyte retrieval) supplemented with 10% (v/v) FBS, 2 mM $NaHCO_3$, 5 mg/ml BSA (Invitrogen, Carlsbad, Calif.).

TABLE 1

| Medium for oocyte retrieval | |
|---|---|
| Ingredient | Content |
| TCM powder 1 L (Gibco 31100-027) | 9.9 g |
| P/S antibiotics | 1% (penicillin 10000 IU, streptomycin 10 mg) |
| HEPES buffer | 2.38 g |
| FBS | 10% (v/v) |
| $NaHCO_3$ | 0.1680 g |
| BSA | 5 mg/L |

Embodiment 2

Enucleation of Recipient Oocytes 0.1% (v/v) hyaluronidase (Sigma, USA) was added to an hCR2aa medium (see Table 2) prepared by adding Hepes-buffer to $Ca^{2+}$-free CR2 medium (Charles Rosenkrans 2; Rosenkrans et al., Biol. Reprod. 49, 459-462, 1993). Cumulus cells from the oocytes obtained in embodiment 1 were then removed by repeated pipetting in the above medium. The oocytes were then stained with 5 μg/mL bisbenzimide (Hoechst 33342) for 5 minutes and observed under an inverted microscope equipped with epiflu-orescence at 200× magnification so as to select only oocytes with the first polar body. 10% (v/v) FBS and 5 μg/ml cytochalasin B were added to an hCR2aa medium (see Table 3), and the selected oocytes were enucleated in the medium using a micromanipulator (Narishige, Tokyo, Japan). That is, the oocytes were held with a holding micropipette (inner diameter; 150 μm), and then the first polar body, adjacent cytoplasm (less than 5%), and oocyte nuclei were removed using an aspiration pipette. The enucleated oocytes were stored in a TCM-199 medium (see Table 4) supplemented with 10% (v/v) FBS.

TABLE 2

| Composition of CR2 medium | | | |
|---|---|---|---|
| Ingredient | | | Content |
| NaCl | 3.1 g/50 ml | mCR2-S | 4 ml |
| KCl | 0.1050 g | | |
| $KH_2PO_4$ | 0.0230 g | | |
| hemiCa-lactate | 0.1360 g | | |
| P/S | 5 ml | | |
| Phenol-red | 400 μl | | |
| $NaHCO_3$ | 1.0531 g/50 ml | St-B | 640 μl |
| | NEAA | | 400 μl |
| Glycine | 0.0275 g/10 ml | Glycine | 400 μl |
| | BSA | | 0.12 g |

TABLE 3

Composition of hCR2aa medium

| Ingredient | Content | | |
|---|---|---|---|
| NaCl | 3.1 g/50 ml | mCR2-S | 4 ml |
| KCl | 0.1050 g | | |
| KH$_2$PO$_4$ | 0.0230 g | | |
| hemiCa-lactate | 0.1360 g | | |
| P/S | 5 ml | | |
| Phenol-red | 400 µl | | |
| NaHCO$_3$ | 1.0531 g/50 ml | St-B | 640 µl |
| HEPES | 0.5958 g/10 ml | St-E | 1680 µl |
| NEAA | | | 400 µl |
| Glycine | 0.0275 g/10 ml | Glycine | 400 µl |
| BSA | | | 0.12 g |

TABLE 4

Composition of TCM-199 medium
TCM-199 medium

| Ingredient | Content |
|---|---|
| TCM199 liquid | 89 ml |
| pyruvic acid | 0.0099 g |
| P/S (antibiotics) | 1 ml |
| FBS | 10% |

Embodiment 3

Preparation of Nuclear Donor Cells

Adult fibroblasts collected from dogs were used as nuclear donor cells. To this end, an ear skin biopsy from a male Afghan Hound (2-mo old) was first isolated. Small pieces of the ear tissue fragment were washed three times in DPBS (Dulbecco's Phosphate Buffered Saline) and minced with a surgical blade. The minced tissue was dissociated in Dulbecco's modified Eagle's medium (DMEM; Life Technologies, Rockville, Md.) containing 0.25% (w/v) trypsin and 1 mM EDTA for 1 hour at 37° C. The trypsinized cells were washed once in Ca$^{2+}$ and Mg$^{2+}$-free DPBS by centrifugation at 300×g for 2 minutes, and seeded into 60-mm plastic culture dishes (Becton Dickinson, Lincoln Park, N.J.). The seeded cells were subsequently cultured for 6 to 8 days in DMEM supplemented with 10% (v/v) FBS, 1 mM glutamine, 25 mM NaHCO$_3$ and 1% (v/v) minimal essential medium (MEM) non-essential amino acid solution (Invitrogen, CA) at 39° C. in a humidified atmosphere of 5% CO$_2$ and 95% air. After removal of unattached cells, attached cells were trypsinized for 1 minute in a medium containing 0.1% trypsin and 0.02% EDTA and then were put into three new culture dishes for additional subculture at intervals of 4 to 6 days. The subcultured cells were then placed in a freezing medium composed of 80% (v/v) DMEM, 10% (v/v) DMSO and 10% (v/v) FBS and were stored in liquid nitrogen at −196° C. 3 to 8 successive generations of cells were used for the somatic cell nuclear transfer and were thawed before performing the somatic cell nuclear transfer. And, they were cultured for 3 to 4 days until they got confluency and trypsinized for about 1 minute to retrieve the cells from the monolayer.

Embodiment 4

Microinjection and Fusion of Nuclear Donor Cells into Enucleated Oocytes

The nuclear donor cells prepared in embodiment 3 were microinjected into the enucleated oocytes prepared in embodiment 2. The nuclear donor cells were microinjected into a perivitellin space of the enucleated oocytes. After an aspiration pipette on the micromanipulator of embodiment 2 was replaced with a transfer pipette, the fixed enucleated oocytes were treated with 100 mg/mL of phytohemagglutinin in hCR2aa medium and the slit of the enucleated oocytes was held with a holding pipette and then was inserted with a transfer pipette to inject fibroblasts isolated as single cells in embodiment 3 between the zona pellucida and the cytoplasm of the enucleated oocytes. The nuclear donor cells-oocytes couplets were then placed in a fusion medium (containing 0.26 M mannitol, 0.1 mM MgSO$_4$, 0.5 mM Hepes and 0.05% BSA), and put between two parallel electrodes attached to the manipulation device (Nikon-Narishige, Japan), and electrical stimulus was applied by an Electro-Cell fusion apparatus (NEPA, GENE Co., Chiba, Japan). In this case, needle-type electrodes were used, and a distance between the electrodes was about 180 µm (diameter of oocyte). Two pulses of 4.0 kv/cm were applied for 15 µs, and after one hour of electrical stimulation, fusion of oocyte cytoplasm and nuclear donor cell was observed using a stereomicroscope. 167 of the fused nuclear transfer embryos were selected and cultured for 3 hours in a modified synthetic oviductal fluid (mSOF) (see table 5) (G. Jang et al., Reprod. Fertil. Dev., 15, 179-185, 2003). The present inventors have named the prepared nuclear transfer embryos SNU-BONA (cloned embryos), and have deposited them with an international depositary authority, KCTC (Korean Collection for Type Cultures; Korean Research Institute of Bioscience and Biotechnology, 52, Eoeun-dong, Yuseong-gu, Daejeon, Korea) on Nov. 27, 2006, under the accession number KCTC 11037BP.

TABLE 5

Composition of mSOF

| Ingredient | | | Concentration | Volume |
|---|---|---|---|---|
| NaCl(54.44) | 2.900-3.100 g/ml | Stock-T | 107.7 mM(3.14 g) | 2 ml |
| KCl(74.55) | 0.2669 g | | 7.2 mM | |
| KH$_2$PO$_4$(136.1) | 0.0810 g | | 1.2 mM | |
| Sod. Lactate | 0.28 ml | | 3.3 mM | |
| Kanamycin | 0.0375 g | | | |
| Phenol-Red | 0.0050 g | | | |
| NaHCO$_3$(84.01) | 1.0531 g/50 ml | Stock-B | 25.1 mM | 2 ml |
| | 0.42124 g/20 ml | | | |
| Sod. Pyruvate(110.0) | 0.0182 g/5 ml | Stock-C | 0.3 mM | 200 µl |
| MgCl$_2$6H$_2$O(147.0) | 0.0996 g/10 ml | Stock-M | 0.5 mM | 200 µl |
| CaCl$_2$2H$_2$O(203.3) | 0.2514 g/10 ml | Stock-D | 1.71 mM | 200 µl |
| Glucose(180) | 0.27024 g/10 ml | | 1.5 mM | 200 µl |

TABLE 5-continued

Composition of mSOF

| Ingredient | Concentration | | Volume |
|---|---|---|---|
| Glutamine(146.1) | 0.14618 g/10 ml | | 1 mM | 200 μl |
| Citri Acid(192) | 0.096 g/10 ml | Stock-CA | 0.5 mM | 200 μl |
| HEPES(238.3) | 0.5958 g/10 ml | Stock-E | 2.5 mM | 200 μl |
| EAA(Gibco 11051-018) | | | | 400 μl |
| NEAA(Gibco 11140-019) | | | | 200 μl |
| ITS(I-3146) | | | | 100 μl |
| BSA(fatty acid free) | | | | 0.1600 g |
| Hyaluronic Acid | | | 0.5 mg/ml | |
| 1N NaOH | | | | |
| D. W. | | | | 총 20 ml | pH 7.2-7.4
Osmotic pressure: 275-285
Be careful: EAA, NEAA are sensitive to light.

Embodiment 5

Activation of Nuclear Transfer Embryos

The nuclear transfer embryos obtained in embodiment 4 were cultured in mSOF containing 10 μM ionophore for 4 minutes at 39° C. for activation. The embryos were then washed and further incubated for 4 hours in mSOF supplemented with 1.9 mM of 6-dimethylaminopurine (see table 5).

The nuclear transfer embryos were cultured in 25 μl microdrops of mSOF overlaid with mineral oil before the embryos were transferred into surrogate mothers.

Embodiment 6

Embryo Transfer into Surrogate Mothers and Production of Cloned Dogs 167 nuclear transfer embryos of embodiment 5 were surgically transferred into the oviduct of naturally estrous surrogate mothers about 72 hours after ovulation. The transfer was conducted within 4 hours after the activation of the nuclear transfer embryos. 12 mongrel dogs were used as the surrogate mothers who were disease-free and had the repetition of the normal estrus cycle and a normal uterine condition. To this end, the surrogate mothers were first anesthetized by vascular injection with 0.1 mg/kg acepromazine and 6 mg/kg propofol, and maintained in the anesthetized state using 2% isoflurane. The operation area of the anesthetized female dog was aseptically operated on and incised at the center of the abdomen in a general laparotomy so as to expose the oviduct. The abdominal cavity was stimulated by hand to draw the ovarium, oviduct, and uterus toward the incision. The mesovarium of the drawn ovarium was carefully handled to recognize the opening of the oviduct, and a 3.5F Tom cat catheter (Sherwood, St. Louis, Mo.) equipped with a 1.0 ml tuberculin syringe (Latex free, Becton Dickinson & CO. Franklin lakes, NJ 07417) was inserted into the oviduct to secure a sufficient space in the front of the catheter. Then, the nuclear transfer embryos were injected into the oviduct through the catheter. Whether the nuclear transfer embryos were successfully injected was observed under a microscope, and 500 ml physiological saline containing an antibiotic was injected into the abdominal cavity. The abdominal suture was performed with an absorbable suture, and then a skin suture was performed. To prevent post-surgery infection, a broad range of antibiotics were injected for 3 days. States of transfer to surrogate mothers and numbers of nuclear transfer embryos are shown in table 6 below.

TABLE 6

Surrogate mother, number of oocyte donors, oocyte state, and number of nuclear transfer embryos

| Surrogate mother | Number of oocyte donors | Oocyte state | Number nuclear transfer embryos |
|---|---|---|---|
| A | 2 | All mature | 22 |
| B | 2 | Mature, slightly aged | 20 |
| C | 2 | All mature | 16 |
| D | 4 | 3: immature 1: moderately aged | 10 |
| E | 1 | Mature | 6 |
| F | 1 | Immature | 8 |
| G | 2 | Immature, mature | 16 |
| H | 2 | All slightly aged | 18 |
| I | 1 | Very aged | 8 |
| J | 2 | Immature, mature | 17 |
| K | 2 | Immature, mature | 14 |
| L | 2 | Slightly aged, moderately aged | 12 |
| SUM | 23 | | 167 |

At 23 days after transferring the nuclear transfer embryos into the surrogate mothers, pregnancies were detected using a SONOACE 9900 (Medison Co., LTD., Seoul, Korea) ultrasound scanner attached with a 7.0 MHz linear-array probe. Pregnancy was monitored by ultrasound every 2 weeks after initial confirmation. As a result, it was confirmed that three dogs (surrogate mothers: C, J, K) had become pregnant. That is, it was detected by the ultrasonic wave that one embryonic sac was found from each surrogate mother and there was no fetal death or abortion. The cloned dogs were delivered by cesarean section 60 days after the nuclear transfer embryos were transferred. The respective birth weights were 520 g, 460 g, and 520 g, and all were females and appeared to be normal and healthy (see FIG. 3).

Experimental Example 1

Examination of Genetic Identity of Cloned Dogs Produced According to the Present Invention The 3 cloned dogs obtained in embodiment 6 were examined to check whether they were genetically identical to the donor Afghan Hound which had donated the nuclear cells in embodiment 3 in accordance with the method of the present invention. To this end, genomic DNAs of the cloned dogs, the donor dog, the surrogate recipients and nuclear donor fibroblasts were isolated and a parentage analysis was performed thereon. Blood samples were first collected from the donor dog and the surrogate mother. The genomic DNA was extracted from the blood sample and the trypsinized fibroblasts in accordance with a method provided by the producer of G-spin genome DNA extracting kit (Intron, Korea). The isolated genomic DNA samples were dissolved in 50 μl TE and used to perform microsatellite analysis with 14 canine specific markers (PEZ1, PEZ2, PEZ3, PEZ5, PEZ6, PEZ10, PEZ11, PEZ012, PEZ13, PEZ16, PEZ017, FH2010, FH2054, FH2079). That is, the isolated genomic DNA as a template was PCR-amplified using fluorescently labeled locus-specific primers (see Table 7) prepared based on the sequences of the known markers. The amplification products were analyzed with an automated DNA sequence analyzer (ABI 373: Applied Biosystems, Foster City, Calif.). In addition, proprietary software (GeneScan and Genotyper; Applied Biosystems) was used to estimate the size of the PCR products.

TABLE 7

Primers used for PCR amplification

| Primer | | Sequence | Sequence No. |
|---|---|---|---|
| PEZ001 | Sense | 5'-GGCTGTCACTTTTCCCTTTC-3' | 1 |
| | Anti-sense | 5'-CACCACAATCTCTCTCATAAATAC-3' | 2 |
| PEZ002 | sense | 5'-TCCTCTCTAACTGCCTATGC-3' | 3 |
| | Anti-sense | 5'-GCCCTTGAATATGAACAATGACACTGTATC-3' | 4 |
| PEZ003 | Sense | 5'-CACTTCTCATACCCAGACTC-3' | 5 |
| | Anti-sense | 5'-CAATATGTCAACTATACTTC-3' | 6 |
| PEZ005 | Sense | 5'-GCTATCTTGTTTCCCACAGC-3' | 7 |
| | Anti-sense | 5'-TCACTGTATACAACATTGTC-3' | 8 |
| PEZ006 | Sense | 5'-ATGAGCACTGGGTGTTATAC-3' | 9 |
| | Anti-sense | 5'-ACACAATTGCATTGTCAAAC-3' | 10 |
| PEZ010 | Sense | 5'-CTTCATTGAAGTATCTATCC-3' | 11 |
| | Anti-sense | 5'-CCTGCCTTTGTAAATGTAAG-3' | 12 |
| PEZ011 | Sense | 5'-ATTCTCTGCCTCTCCCTTTG-3' | 13 |
| | Anti-sense | 5'-TGTGGATAATCTCTTCTGTC-3' | 14 |
| PEZ012 | Sense | 5'-GTAGATTAGATCTCAGGCAG-3' | 15 |
| | Anti-sense | 5'-TAGGTCCTGGTAGGGTGTGG-3' | 16 |
| PEZ013 | Sense | 5'-AGTCTGGTGATTTAATTCGG-3' | 17 |
| | Anti-sense | 5'-GTCTAGTCCCCAGTCTAGTTCACTGCCC-3' | 18 |
| PEZ016 | Sense | 5'-GCTCTTTGTAAAATGACCTG-3' | 19 |
| | Anti-sense | 5'-GTGGGAATCGTCCTAAAACCC-3' | 20 |
| PLZ017 | Sense | 5'-CTAAGGGACTGAACTTCTCC-3' | 21 |
| | Anti-sense | 5'-GTGGAACCTGCTTAAGATTC-3' | 22 |
| FH2010 | Sense | 5'-AAATGGAACAGTTGAGCATGC-3' | 23 |
| | Anti-sense | 5'-CCCCTTACAGCTTCATTTTCC-3' | 24 |
| FH2054 | Sense | 5'-GCCTTATTCATTGCAGTTAGGG-3' | 25 |
| | Anti-sense | 5'-ATGCTGAGTTTTGAACTTTCCC-3' | 26 |
| FH2079 | Sense | 5'-CAGCCGAGCACATGGTTT-3' | 27 |
| | Anti-sense | 5'-ATTGATTCTGATATGCCCAGC-3' | 28 |

As a result of experiment, it was confirmed that all of the three cloned dogs produced by the method of the present invention were genetically identical to the donor Afghan Hound and the fibroblasts isolated from the donor dog. Conversely, it was confirmed that the cloned dogs of the present invention and the surrogate mothers were genetically distinct from each other (see table 8).

TABLE 8

Results of genotype analysis

| | Donor blood | Donor cell | Cloned dog 1 | Cloned dog 2 | Cloned dog 3 | Surrogate mother of cloned dog 1 | Surrogate mother of cloned dog 2 | Surrogate mother of cloned dog 3 |
|---|---|---|---|---|---|---|---|---|
| PEZ01 | 118/118 | 118/118 | 118/118 | 118/118 | 118/118 | 114/118 | 114/118 | 114/118 |
| PEZ02 | 121/121 | 121/121 | 121/121 | 121/121 | 121/121 | 117/121 | 117/117 | 117/125 |

TABLE 8-continued

Results of genotype analysis

|  | Donor blood | Donor cell | Cloned dog 1 | Cloned dog 2 | Cloned dog 3 | Surrogate mother of cloned dog 1 | Surrogate mother of cloned dog 2 | Surrogate mother of cloned dog 3 |
|---|---|---|---|---|---|---|---|---|
| PEZ03 | 127/130 | 127/130 | 127/130 | 127/130 | 127/130 | 123/124 | 123/123 | 137/140 |
| PEZ05 | 105/113 | 105/113 | 105/113 | 105/113 | 105/113 | 105/113 | 101/101 | 101/103 |
| PEZ06 | 180/184 | 180/184 | 180/184 | 180/184 | 180/184 | 177/179 | 187/187 | 171/181 |
| PEZ10 | 264/276 | 264/276 | 264/276 | 264/276 | 264/276 | 287/287 | 280/280 | 287/287 |
| PEZ11 | 128/146 | 128/146 | 128/146 | 128/146 | 128/146 | 132/136 | 124/128 | 125/132 |
| PLZ12 | 271/282 | 271/282 | 271/282 | 271/282 | 271/282 | 271/271 | 292/300 | nd* |
| PLZ13 | 174/217 | 174/217 | 174/217 | 174/217 | 174/217 | 174/221 | 174/221 | 217/221 |
| PLZ16 | 288/300 | 288/300 | 288/300 | 288/300 | 288/300 | 284/300 | 308/308 | 300/304 |
| PLZ17 | 207/207 | 207/207 | 207/207 | 207/207 | 207/207 | 203/207 | 199/203 | 199/207 |
| FH2010 | 227/228 | 227/228 | 227/228 | 227/228 | 227/228 | 228/236 | 227/231 | 223/231 |
| FH2054 | 151/155 | 151/155 | 151/155 | 151/155 | 151/155 | 151/151 | 167/167 | 155/167 |
| FH2079 | 269/269 | 269/269 | 269/269 | 269/269 | 269/269 | 273/273 | 273/273 | 273/273 |

*Allele is not determined.

Experimental Example 2

Efficiency of Cloning a Dog According to the Method of the Present Invention

According to the embodiments of producing a cloned dog of the present invention, 167 nuclear transfer embryos were used to produce 3 cloned dogs from their surrogate mothers. In contrast, according to the conventional method for producing a cloned dog that is well known in the art (see Korean Patent Application No. 2005-67736), 1095 nuclear transfer embryos were used to produce 2 cloned dogs from 123 surrogate mothers, and one of them survived and the other died. Therefore, it was confirmed that the method of the present invention can produce a cloned dog with significantly higher efficiency than the conventional method.

The method of the present invention has the effect of producing a cloned dog with high efficiency, and thus can contribute to the development of studies in veterinary medicine, anthropology and medical science, such as the propagation of superior species, xenotransplantation and diseased animal models. In addition, the present invention has the effect of exactly researching production properties of the cloned dog by producing a female cloned dog for the first time, rather than the conventional male cloned dog.

While the invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A nuclear transfer embryo deposited under accession number KCTC 11037BP.

2. A method for producing a cloned dog, comprising:
producing an enucleated oocyte of a dog;
producing a nuclear donor cell of a dog;
micro-injecting and electrofusing the nuclear donor cell, wherein the electrofusion is carried out under a condition of 3.8 to 4.2 kV/cm;
activating the electrofused oocyte and producing a nuclear transfer embryo; and
transferring the nuclear transfer embryo into an oviduct of a surrogate mother of a dog to give birth to living offspring;
wherein efficiency of producing a cloned dog relative to the number of nuclear transfer embryos is about 1.8% and the surrogate mother is a dog.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: PEZ001 sense primer

<400> SEQUENCE: 1
ggctgtcact tttcccttc                                         20

<210> SEQ ID NO 2
<211> LENGTH: 24
<212> TYPE: DNA
<213> ORGANISM: Artificial Sequence
<220> FEATURE:
<223> OTHER INFORMATION: PEZ001 antisens primer

<400> SEQUENCE: 2
caccacaatc tctctcataa atac                                   24

<210> SEQ ID NO 3
<211> LENGTH: 20
<212> TYPE: DNA
<213> ORGANISM: Artificial Sequence
<220> FEATURE:
<223> OTHER INFORMATION: PEZ002 sense primer

```
<400> SEQUENCE: 3
tcctctctaa ctgcctatgc                                                  20

<210> SEQ ID NO 4
<211> LENGTH: 30
<212> TYPE: DNA
<213> ORGANISM: Artificial Sequence
<220> FEATURE:
<223> OTHER INFORMATION: PEZ002 antisens primer

<400> SEQUENCE: 4
gcccttgaat atgaacaatg acactgtatc                                       30

<210> SEQ ID NO 5
<211> LENGTH: 20
<212> TYPE: DNA
<213> ORGANISM: Artificial Sequence
<220> FEATURE:
<223> OTHER INFORMATION: PEZ003 sense primer

<400> SEQUENCE: 5
cacttctcat acccagactc                                                  20

<210> SEQ ID NO 6
<211> LENGTH: 20
<212> TYPE: DNA
<213> ORGANISM: Artificial Sequence
<220> FEATURE:
<223> OTHER INFORMATION: PEZ003 antisense primer

<400> SEQUENCE: 6
caatatgtca actatacttc                                                  20

<210> SEQ ID NO 7
<211> LENGTH: 20
<212> TYPE: DNA
<213> ORGANISM: Artificial Sequence
<220> FEATURE:
<223> OTHER INFORMATION: PEZ005 sense primer

<400> SEQUENCE: 7
gctatcttgt ttcccacagc                                                  20

<210> SEQ ID NO 8
<211> LENGTH: 20
<212> TYPE: DNA
<213> ORGANISM: Artificial Sequence
<220> FEATURE:
<223> OTHER INFORMATION: PEZ005 antisense primer

<400> SEQUENCE: 8
tcactgtata caacattgtc                                                  20

<210> SEQ ID NO 9
<211> LENGTH: 20
<212> TYPE: DNA
<213> ORGANISM: Artificial Sequence
<220> FEATURE:
<223> OTHER INFORMATION: PEZ006 sense primer

<400> SEQUENCE: 9
atgagcactg ggtgttatac                                                  20

<210> SEQ ID NO 10
<211> LENGTH: 20
```

```
<212> TYPE: DNA
<213> ORGANISM: Artificial Sequence
<220> FEATURE:
<223> OTHER INFORMATION: PEZ006 antisense primer

<400> SEQUENCE: 10
acacaattgc attgtcaaac                                                 20

<210> SEQ ID NO 11
<211> LENGTH: 20
<212> TYPE: DNA
<213> ORGANISM: Artificial Sequence
<220> FEATURE:
<223> OTHER INFORMATION: PEZ010 sense primer

<400> SEQUENCE: 11
cttcattgaa gtatctatcc                                                 20

<210> SEQ ID NO 12
<211> LENGTH: 20
<212> TYPE: DNA
<213> ORGANISM: Artificial Sequence
<220> FEATURE:
<223> OTHER INFORMATION: PEZ010 antisense primer

<400> SEQUENCE: 12
cctgcctttg taaatgtaag                                                 20

<210> SEQ ID NO 13
<211> LENGTH: 20
<212> TYPE: DNA
<213> ORGANISM: Artificial Sequence
<220> FEATURE:
<223> OTHER INFORMATION: PEZ011 sense primer

<400> SEQUENCE: 13
attctctgcc tctccctttg                                                 20

<210> SEQ ID NO 14
<211> LENGTH: 20
<212> TYPE: DNA
<213> ORGANISM: Artificial Sequence
<220> FEATURE:
<223> OTHER INFORMATION: PEZ011 antisense primer

<400> SEQUENCE: 14
tgtggataat ctcttctgtc                                                 20

<210> SEQ ID NO 15
<211> LENGTH: 20
<212> TYPE: DNA
<213> ORGANISM: Artificial Sequence
<220> FEATURE:
<223> OTHER INFORMATION: PEZ012 sense primer

<400> SEQUENCE: 15
gtagattaga tctcaggcag                                                 20

<210> SEQ ID NO 16
<211> LENGTH: 20
<212> TYPE: DNA
<213> ORGANISM: Artificial Sequence
<220> FEATURE:
<223> OTHER INFORMATION: PEZ012 antisense primer

<400> SEQUENCE: 16
taggtcctgg tagggtgtgg                                                 20
```

<210> SEQ ID NO 17
<211> LENGTH: 20
<212> TYPE: DNA
<213> ORGANISM: Artificial Sequence
<220> FEATURE:
<223> OTHER INFORMATION: PEZ013 sense primer

<400> SEQUENCE: 17
agtctggtga tttaattcgg                                            20

<210> SEQ ID NO 18
<211> LENGTH: 28
<212> TYPE: DNA
<213> ORGANISM: Artificial Sequence
<220> FEATURE:
<223> OTHER INFORMATION: PEZ013 antisens primer

<400> SEQUENCE: 18
gtctagtccc cagtctagtt cactgccc                                   28

<210> SEQ ID NO 19
<211> LENGTH: 20
<212> TYPE: DNA
<213> ORGANISM: Artificial Sequence
<220> FEATURE:
<223> OTHER INFORMATION: PEZ016 sense primer

<400> SEQUENCE: 19
gctctttgta aaatgacctg                                            20

<210> SEQ ID NO 20
<211> LENGTH: 21
<212> TYPE: DNA
<213> ORGANISM: Artificial Sequence
<220> FEATURE:
<223> OTHER INFORMATION: PEZ016 antisense primer

<400> SEQUENCE: 20
gtgggaatcg tcctaaaacc c                                          21

<210> SEQ ID NO 21
<211> LENGTH: 20
<212> TYPE: DNA
<213> ORGANISM: Artificial Sequence
<220> FEATURE:
<223> OTHER INFORMATION: PEZ017 sense primer

<400> SEQUENCE: 21
ctaagggact gaacttctcc                                            20

<210> SEQ ID NO 22
<211> LENGTH: 20
<212> TYPE: DNA
<213> ORGANISM: Artificial Sequence
<220> FEATURE:
<223> OTHER INFORMATION: PEZ017 antisense primer

<400> SEQUENCE: 22
gtggaacctg cttaagattc                                            20

<210> SEQ ID NO 23
<211> LENGTH: 21
<212> TYPE: DNA
<213> ORGANISM: Artificial Sequence
<220> FEATURE:
<223> OTHER INFORMATION: FH2010 sense primer

<400> SEQUENCE: 23
aaatggaaca gttgagcatg c                                              21

<210> SEQ ID NO 24
<211> LENGTH: 21
<212> TYPE: DNA
<213> ORGANISM: Artificial Sequence
<220> FEATURE:
<223> OTHER INFORMATION: FH2010 antisense primer

<400> SEQUENCE: 24
ccccttacag cttcattttc c                                              21

<210> SEQ ID NO 25
<211> LENGTH: 22
<212> TYPE: DNA
<213> ORGANISM: Artificial Sequence
<220> FEATURE:
<223> OTHER INFORMATION: FH2054 sense primer

<400> SEQUENCE: 25
gccttattca ttgcagttag gg                                             22

<210> SEQ ID NO 26
<211> LENGTH: 22
<212> TYPE: DNA
<213> ORGANISM: Artificial Sequence
<220> FEATURE:
<223> OTHER INFORMATION: FH2054 antisense primer

<400> SEQUENCE: 26
atgctgagtt ttgaactttc cc                                             22

<210> SEQ ID NO 27
<211> LENGTH: 18
<212> TYPE: DNA
<213> ORGANISM: Artificial Sequence
<220> FEATURE:
<223> OTHER INFORMATION: FH2079 sense primer

<400> SEQUENCE: 27
cagccgagca catggttt                                                  18

<210> SEQ ID NO 28
<211> LENGTH: 21
<212> TYPE: DNA
<213> ORGANISM: Artificial Sequence
<220> FEATURE:
<223> OTHER INFORMATION: FH2079 antisense primer

<400> SEQUENCE: 28
attgattctg atatgcccag c                                              21